United States Patent [19]

Enfors

[11] 4,374,013
[45] Feb. 15, 1983

[54] OXYGEN STABILIZED ENZYME ELECTRODE

[76] Inventor: Sven-Olof Enfors, Markörvägen 2, S-191 41 Sollentuna, Sweden

[21] Appl. No.: 239,979

[22] Filed: Mar. 3, 1981

[30] Foreign Application Priority Data

Mar. 6, 1980 [SE] Sweden ............................. 8001711

[51] Int. Cl.³ ........................................... C12Q 1/26
[52] U.S. Cl. ............................. 204/195 B; 204/1 T; 204/195 P; 435/817
[58] Field of Search ............ 435/817; 204/1 E, 195 P, 204/195 B

[56] References Cited

U.S. PATENT DOCUMENTS 3,539,455  11/1970  Clark .................................. 204/1 T
3,919,052  11/1975  Fresnel et al. .............. 204/195 B X
4,016,044   4/1977  Fresnel et al. .............. 204/195 B X

OTHER PUBLICATIONS

Williams et al., "Electrochemical-Enzymatic Analysis of Blood Glucose and Lactate", Analytical Chemistry, vol. 42, No. 1, Jan. 1970, pp. 118-121.
Romette et al., "Glucose-Oxidase Electrode, Measurements of Glucose in Samples Exhibiting High Variability in Oxygen Content", Clinica Chimica Acta, 95, (1979), pp. 249-253.
Enfors et al., "Enzyme Electrodes for Fermentation Control", Process Biochemistry, vol. 13, No. 2, 1978.
Keyes et al., "Glucose Analysis Utilizing Immobilized Enzymes", Enzyme Microb. Technol., 1979, vol. 1, Apr., pp. 91-94.
Guilbault et al., "An Enzyme Electrode for the Amperometric Determination of Glucose", Analytica Chimica Acta, 64, (1973), pp. 439-455.

Primary Examiner—G. L. Kaplan
Attorney, Agent, or Firm—Fisher, Christen & Sabol

[57] ABSTRACT

An enzyme electrode based on an oxygen electrode and an oxygen consuming enzyme is described. The oxygen demand of the electrode is satisfied through an electrolytical oxygen production by means of an anode located close to the enzyme and the sensitive surface of the oxygen electrode. The deviation from a reference value, which could be constant or be formed by the signal from an enzymatically passive oxygen electrode, of the oxygen electrode signal, is used to control the electrolysis current in order to keep the oxygen activity in the enzyme electrode constant. The electrolysis current is used as a measure of the concentration of the substrate of the enzyme.

10 Claims, 2 Drawing Figures

OXYGEN STABILIZED ENZYME ELECTRODE

BACKGROUND OF THE INVENTION

1. Field of the Invention

The present invention refers to an enzyme electrode, the oxygen supply of which is satisfied through electrolysis.

2. Description of the Prior Art

An enzyme electrode is an electrode for quantitative chemical analysis. It consists of an electrochemical sensor (base sensor) the sensitive surface of which is coated with an immobilized enzyme. Usually, the enzyme is separated from the surrounding sample by means of a semi-permeable membrane which permits small molecules to pass but prevents leakage of the enzyme out from the electrode and protects the enzyme from a microbial attack of the sample.

The enzyme is chosen so as to react with the substance to be analyzed. This substance thus forms a substrate for the enzyme. The electrochemical sensor is chosen so as to measure the concentration or activity of any of the reagents of the enzyme reaction. When such an enzyme electrode is introduced into a solution containing the substrate of the enzyme, the substrate molecule diffuses into the enzyme layer and reacts with the enzyme. The reaction products diffuse out from the enzyme layer. The base sensor measures the concentration of one of the reagents in the enzyme layer. After a while an equilibrium is formed where the concentration of the reagents is constant at the surface of the base sensor. If the enzyme activity is sufficiently high as compared to the substrate concentrations of the enzyme layer, the concentration of the reagents will be directly proportional to the substrate concentration of the sample. The base sensor thus indirectly measures the concentration of the substrate of the enzyme in the sample. A more detailed description of the principle of the enzyme electrode and a list of enzyme electrodes known per se are given in Enfors, S-O. and Molin, N., *Process Biochemistry*, Vol. 13, pp. 9–11 and 24 (1978).

During the short period of existence of enzyme electrodes (about 10 years), big efforts have been made to design electrodes for analysis of glucose and other saccharides. Several glucose electrodes are described in the literature.

Their function is usually based on the following reaction:

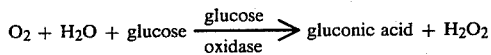

$$O_2 + H_2O + glucose \xrightarrow{glucose\ oxidase} gluconic\ acid + H_2O_2 \quad (I)$$

As $H_2O_2$ could have an inhibiting effect on the glucose oxidase one could possibly coimmobilize catalase with the glucose oxidase whereby the following reaction is added:

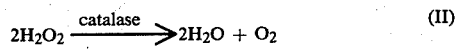

$$2H_2O_2 \xrightarrow{catalase} 2H_2O + O_2 \quad (II)$$

This reaction has the effect that half of the oxygen consumed in reaction (I) is recycled.

As a base sensor for the glucose electrode three different electrodes have been used: an oxygen electrode, a hydrogen peroxide electrode (both these being polarographic electrodes) and a pH electrode. If an oxygen electrode or a pH electrode are used, the glucose electrode could be based merely on reaction (I) or on the reactions (I)+(II). The hydrogen-peroxide electrode as a base sensor will however, require that only reaction (I) takes place, i.e. catalase is not present in the glucose electrode. The pH-based glucose electrode has the disadvantage that the response characteristic varies and is determined by the pH dependence of the buffering capacity of the sample, which results in that the electrode cannot be calibrated in advance for analysis of samples having unknown buffering properties. The sensitivity to glucose and the measuring range of the electrode is then primarily determined by the buffering capacity of the sample. This disadvantage is avoided by choosing one of the other base sensors (oxygen or hydrogenperoxide electrodes), whereby the response of the glucose electrode will be directly proportional to the glucose concentration. The measuring range of these electrodes is determined by the relation of the permeability for glucose and oxygen of the membrane in that a high ratio between the glucose permeability and the oxygen permeability gives an increased sensitivity whereas a small ratio gives a decreased sensitivity but a wider measuring range. At high rates of glucose the total enzyme activity of the electrode could also limit the measuring range as the function of the enzyme electrode requires that the enzymatic reaction is limited by the substrate.

In practice it has proved that the measuring range of all glucose electrodes hitherto used has had an upper limit of 1–2 glucose/l as the oxygen transfer rate to the enzyme will not permit a faster enzyme reaction. If the sample is not saturated with respect to oxygen which is often the case for instance in fermentation media, the measuring range will, because of reduced oxygen transfer rate, be further decreased. It is then not possible to extend the measuring range upwards by reducing the permeability of the membrane by using a thicker membrane as this gives rise to a corresponding relative reduction of the oxygen transfer rate to the enzyme.

SUMMARY OF THE INVENTION

The present invention refers to an enzyme electrode, the oxygen need of which is satisfied by producing oxygen through electrolysis of water by using an anode located close to a base sensor consisting of an oxygen electrode. The oxygen production velocity is adapted to the oxygen consumption rate of the enzyme reaction by using the signal of the base sensor to control the electrolysis current so that the oxygen activity in the enzyme electrode is kept at the same level as the oxygen activity of the sample which is measured by a reference electrode. As a measure of the substrate concentration the electrolysis current is used, this current being directly proportional to the oxygen production rate at the anode of the electrolysis cell.

An enzyme electrode so designed has several advantages as compared to the oxygen based enzyme electrodes hitherto used. It is not dependent on a high oxygen concentration of the sample which is the case in enzyme electrodes, the oxygen supply of which takes place through diffusion from the sample. The electrode could also be used for analysis of samples not containing oxygen if the signal of the reference electrode which is normally used as a reference value when controlling the electrolysis current, is replaced by a constant reference value for the electrolysis control. According to the present invention the measuring range of the enzyme electrode could also be extended to high substrate concentrations, since there will be no shortage of oxygen. The limiting parameter for the measurement will be the enzyme activity, but also this limit could be raised by using the present invention if the enzyme electrode is provided with a membrane having a lower permeability for the substrate. This is possible since the reduced oxygen permeability simultaneously obtained will not affect the properties of the enzyme electrode which is the case in the enzyme electrodes known per se.

BRIEF DESCRIPTION OF THE DRAWINGS

The invention is illustrated in the accompanying drawings wherein.

DETAILED DESCRIPTION OF THE INVENTION

Figure 1:
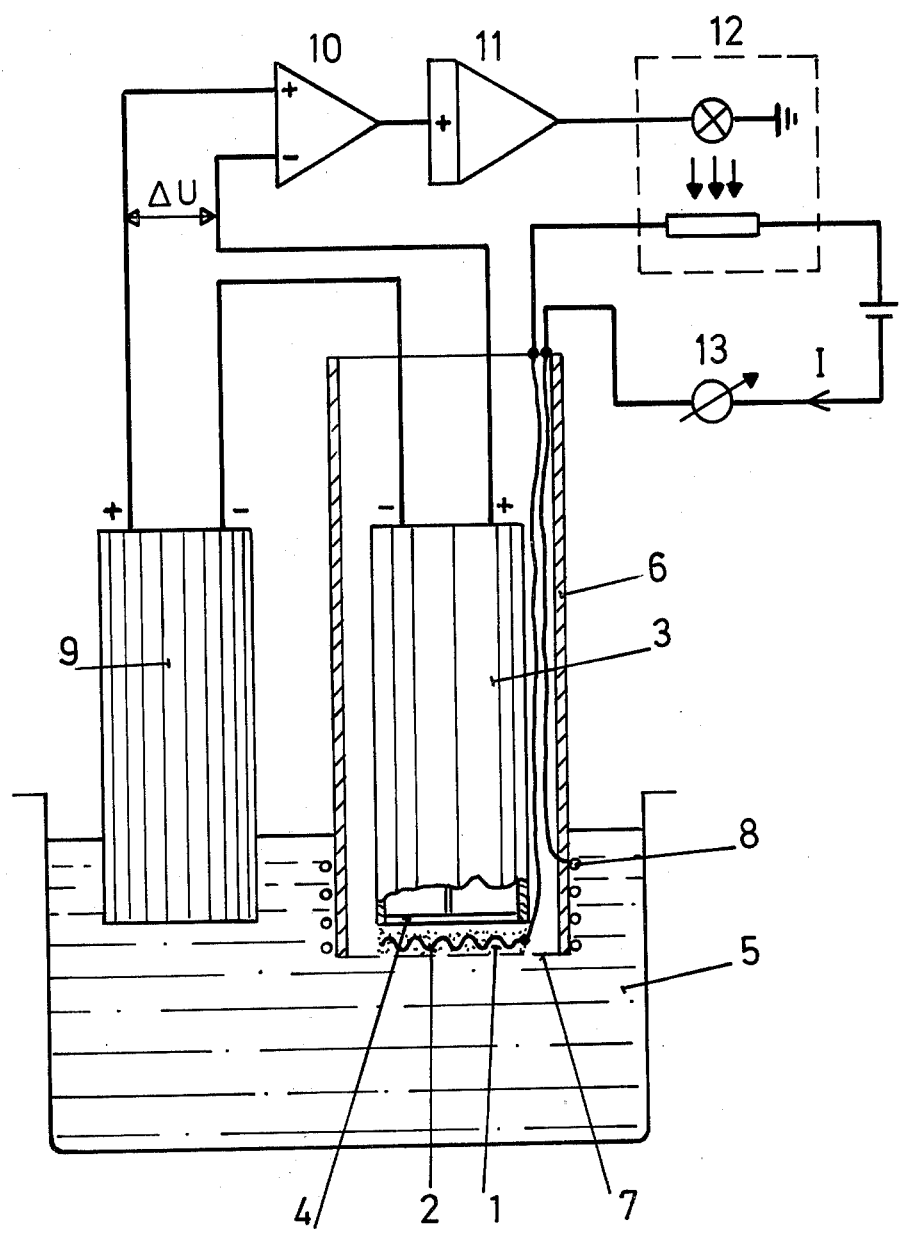
FIG. 1 shows an analytical device which utilizes an enzyme electrode of the present invention.

The enzyme or enzymes 1 are immobilized on an anode 2 which could be formed by a metal network or some other suitable material. This enzyme coated anode is in contact with a gas permeable membrane 4 of an oxygen electrode 3. This basic unit, 1-4, of the electrode could not be sterilized through autoclaving. Furthermore, the enzyme is directly exposed to the sample 5. If it is desirable to separate the enzyme from a direct contact with the sample or an autoclavable electrode is desired, the basic unit could be mounted within an autoclaved tube 6 having a microbetight but glucose permeable membrane 7 in such a way that the enzyme 1 is in contact with the membrane 7. Outside the tube 6 or otherwise in electrolytical contact with the sample 5 a cathode 8 is located, this cathode being formed by a metal thread coil or some other suitable material.

When the substrate diffuses from the sample 5 to the enzyme 1 and reacts, oxygen is consumed which decreases the signal from the oxygen electrode 3. The difference $\Delta U$ which arises between the signal from the oxygen electrode 3 and a reference signal which is the signal from an oxygen electrode 9 in the sample 5 or from a constant voltage supply, controls the electrolysis current I between the anode 2 and the cathode 8. This could for instance be achieved by amplifying the signal $\Delta U$ in an amplifier 10, the amplified signal being supplied to a PI regulator 11 and a current regulator 12 so as to control the current I in order to reduce the difference $\Delta U$ towards 0. The current I is measured by the instrument 13 and constitutes a measure of the amount of oxygen produced per unit of time at the anode 2 in order to maintain a constant oxygen activity in the enzyme 1. The current I thus constitutes a measure of the oxygen consumption rate in the enzyme which is proportional to the glucose concentration of the sample 5.

Figure 2:
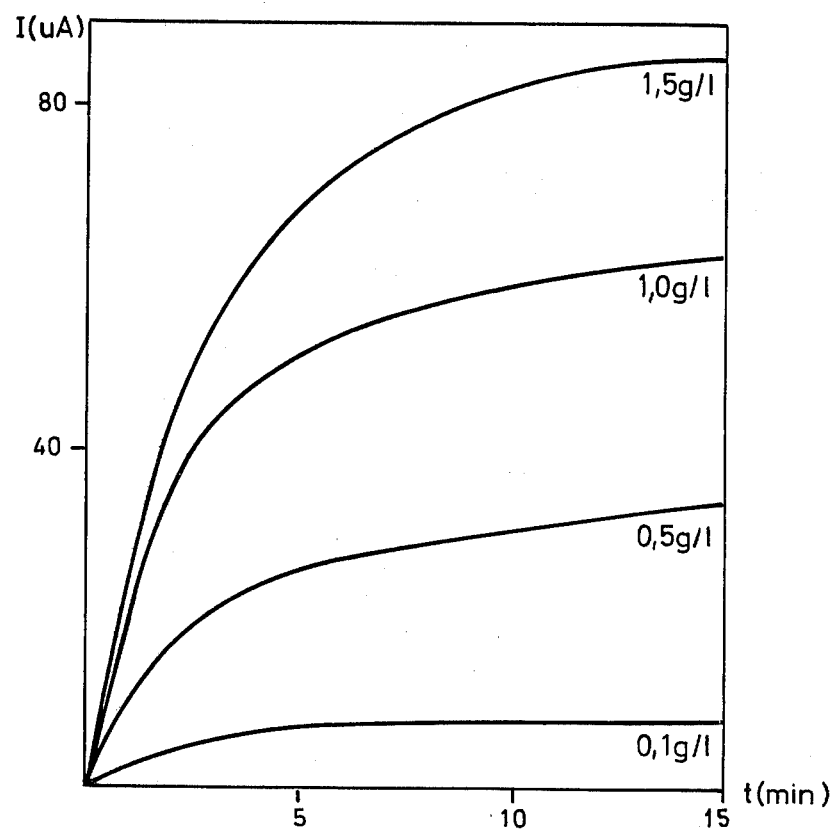
FIG. 2 shows the electrolysis current as a function of time in the analysis of glucose solutions of four concentrations with the device of FIG. 1.

FIG. 2 shows the current I as a function of time when the glucose electrode is introduced in samples containing 0.1–1.5 g glucose/l.

A glucose electrode according to the present invention could be modified for analysis of other saccharides than glucose by coimmobilizing an enzyme which transforms other saccharides or part thereof to glucose with the glucose oxidase in the electrode. An example thereof is the saccharose electrode where $\beta$-fructofuranosidase (invertas), aldosmutarotase and glucose oxidase are coimmobilized. The $\beta$-fructofuranosidase transforms the saccharose to $\alpha$-D-glucose and fructose. The aldomutarotase transforms the $\alpha$-D-glucose to $\beta$-D-glucose which reacts with the glucose oxidase, whereafter the process in the electrode will develop as described above in connection with the glucose electrode.

The present invention could also be used for design of other enzyme electrodes where the oxygen electrode is a base sensor. Examples of such electrodes are alcohol electrodes, cholesterol electrodes and the uric acid electrode, whereby the enzyme alcohol oxidase, cholesterol oxidase and uricase, respectively, are immobilized at the electrolysis anode 2 of the enzyme electrode. Also other oxygen consuming oxidases or oxygenases could be used for the design of an enzyme electrode in accordance with the present invention.

I claim:

1. Enzyme electrode for the analysis of a substrate in a sample comprising:
   (a) an oxygen electrode on which or close to the sensitive surface of which at least one enzyme is immobilized, said oxygen electrode producing a signal responsive to the consumption of oxygen by the reaction between the enzyme and the substrate,
   (b) means for producing a reference signal,
   (c) means for electrolytically producing oxygen by the electrolysis of water, comprising an anode located close to the at least one enzyme, and a cathode,
   (d) means for controlling the electrolysis current between the anode and cathode for producing oxygen in response to the difference between the signal from the oxygen electrode and the reference signal so that the limiting parameter for the enzyme reaction is the enzyme activity, and
   (e) means for measuring the electrolysis current.

2. Enzyme electrode as claimed in claim 1 wherein said at least one enzyme is immobilized on said electrolysis anode.

3. Enzyme electrode as claimed in claim 2 wherein the electrolysis anode is in contact with a gas permeable membrane of said oxygen electrode.

4. Enzyme electrode as claimed in claim 3 wherein the electrolysis anode, the at least one immobilized enzyme, and the oxygen electrode are within a tube, said tube having a membrane which is permeable to said substrate, said electrolysis cathode being in electrolytical contact with the sample.

5. Enzyme electrode as claimed in claim 4 wherein the electrolysis cathode is located outside of the tube.

6. Enzyme electrode as claimed in claim 1 wherein said means for controlling the electrolysis current comprises an amplifier for amplifying the difference in said signals, a PI regulator for the amplified signal, and a current regulator.

7. Enzyme electrode as claimed in claim 1 wherein the means for producing the reference signal is another oxygen electrode which is in said sample.

8. Enzyme electrode as claimed in claim 1 wherein the reference signal is of constant value.

9. Enzyme electrode as claimed in claim 1, 7, or 8 wherein the enzyme at least partly consists of an oxidase or an oxygenase.

10. Enzyme electrode as claimed in claim 5 wherein said means for controlling the electrolysis current maintains a constant oxygen activity in the enzyme, the electrolysis current being controlled so as to reduce said difference towards zero.

* * * * *